United States Patent [19]

Streck et al.

[11] Patent Number: 5,261,880

[45] Date of Patent: Nov. 16, 1993

[54] SINGLE USE SYRINGES WITH SECOND USE LOCKOUT

[75] Inventors: Donald A. Streck, Kailua, Hi.; Thomas C. Kuracina, Ojai; Randall E. Ohnemus, Ventura, both of Calif.

[73] Assignee: Injectimed, Inc., Ventura, Calif.

[21] Appl. No.: 850,463

[22] Filed: Mar. 10, 1992

[51] Int. Cl.$^5$ .............................................. A61M 5/00
[52] U.S. Cl. ...................................... 604/110; 604/232
[58] Field of Search ............... 604/110, 218, 232, 187

[56] References Cited

U.S. PATENT DOCUMENTS

| | | | |
|---|---|---|---|
| 4,878,899 | 11/1989 | Plouff | 604/218 X |
| 4,990,141 | 2/1991 | Byrne et al. | 604/232 X |
| 5,106,372 | 4/1992 | Ranford | 604/218 X |
| 5,120,314 | 6/1992 | Greenwood | 604/110 |

*Primary Examiner*—John D. Yasko
*Attorney, Agent, or Firm*—Donald A. Streck

[57] ABSTRACT

A single-use hypodermic syringe which locks up after one use. There is a body having a cylindrical container for holding a fluid. A hollow needle communicates with an interior of the cylindrical container through one end and a sliding plunger disposed in the cylindrical container is connected to a plunger rod disposed through an opposite end of the cylindrical container. There is locking apparatus allowing the plunger to move only in a direction towards the one end whereby after the plunger is moved adjacent the one end, it cannot be withdrawn for subsequent use. In one version, the plunger has a locking plate attached thereto. In another version, a hooked plate at the end of the cylindrical container digs into and grips an end bore of the plunger. In still another version, the plunger rod is gripped and held if movement to withdraw the plunger is attempted. Both disposable and carpule-using versions are disclosed.

19 Claims, 3 Drawing Sheets

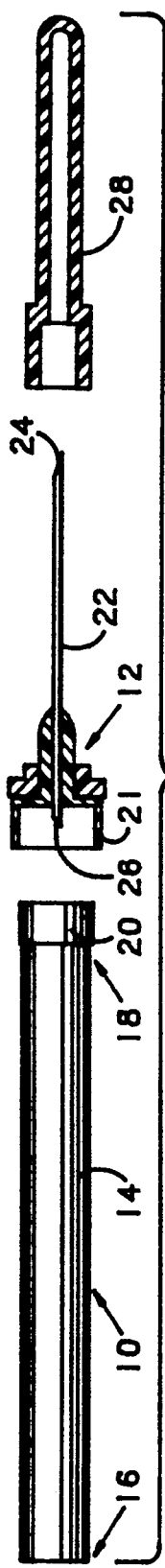
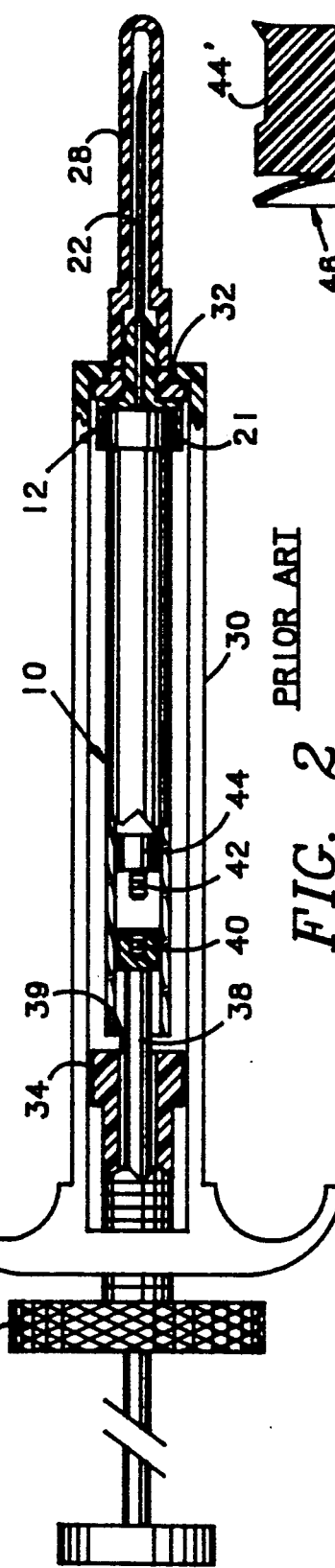
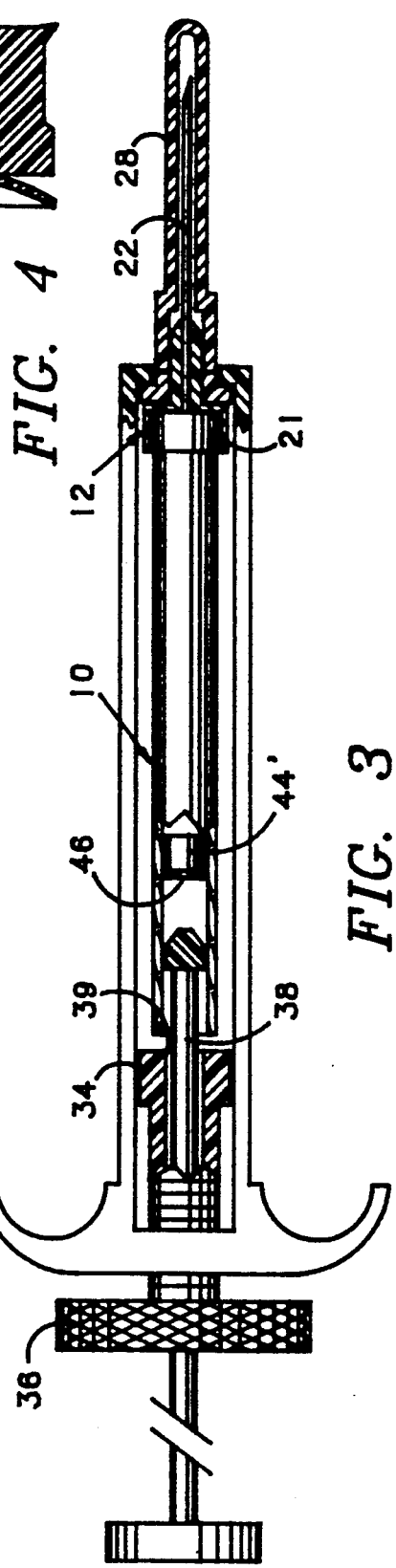

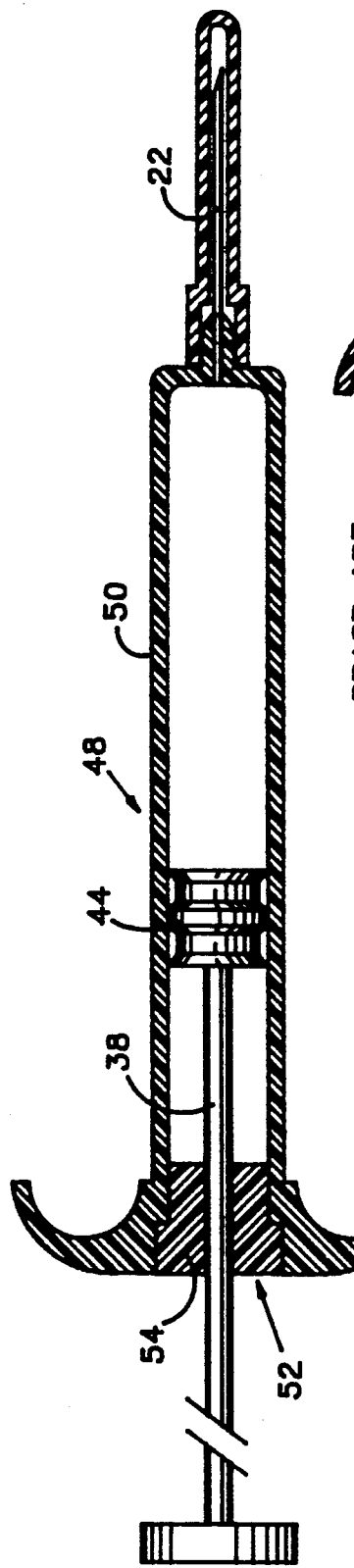
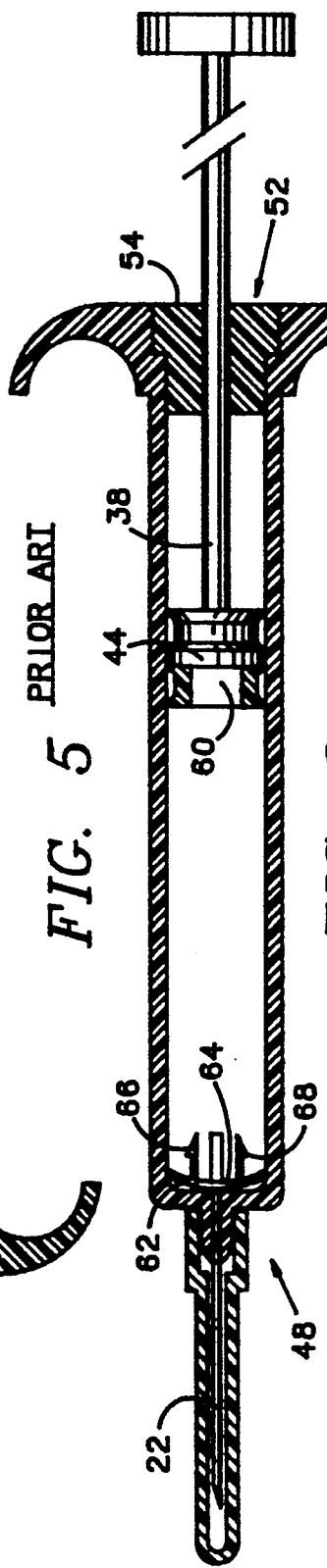
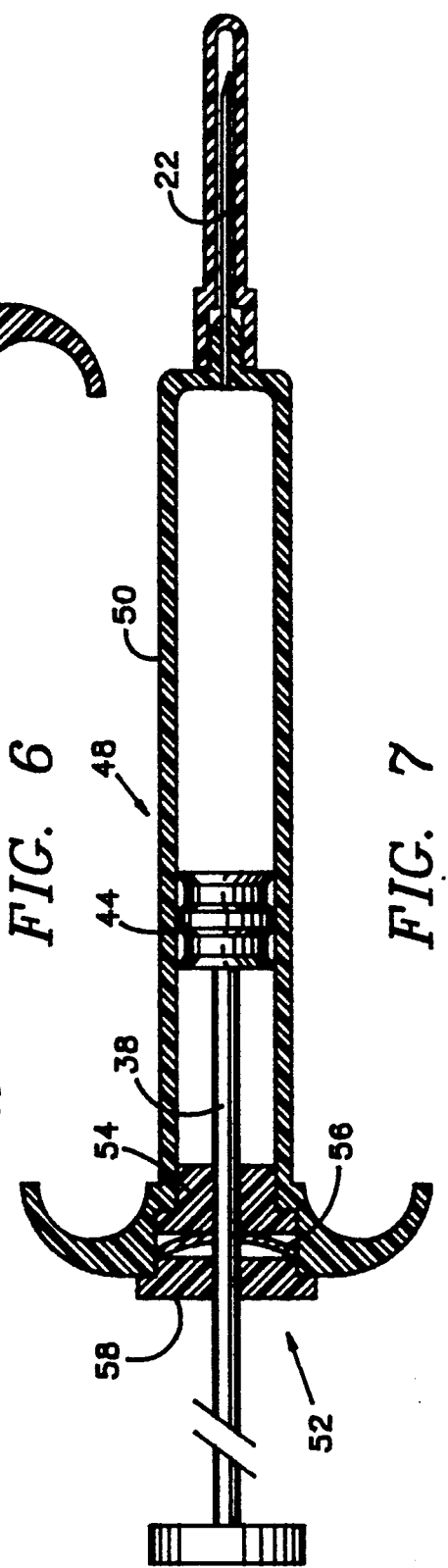
FIG. 5
FIG. 6 PRIOR ART
FIG. 7

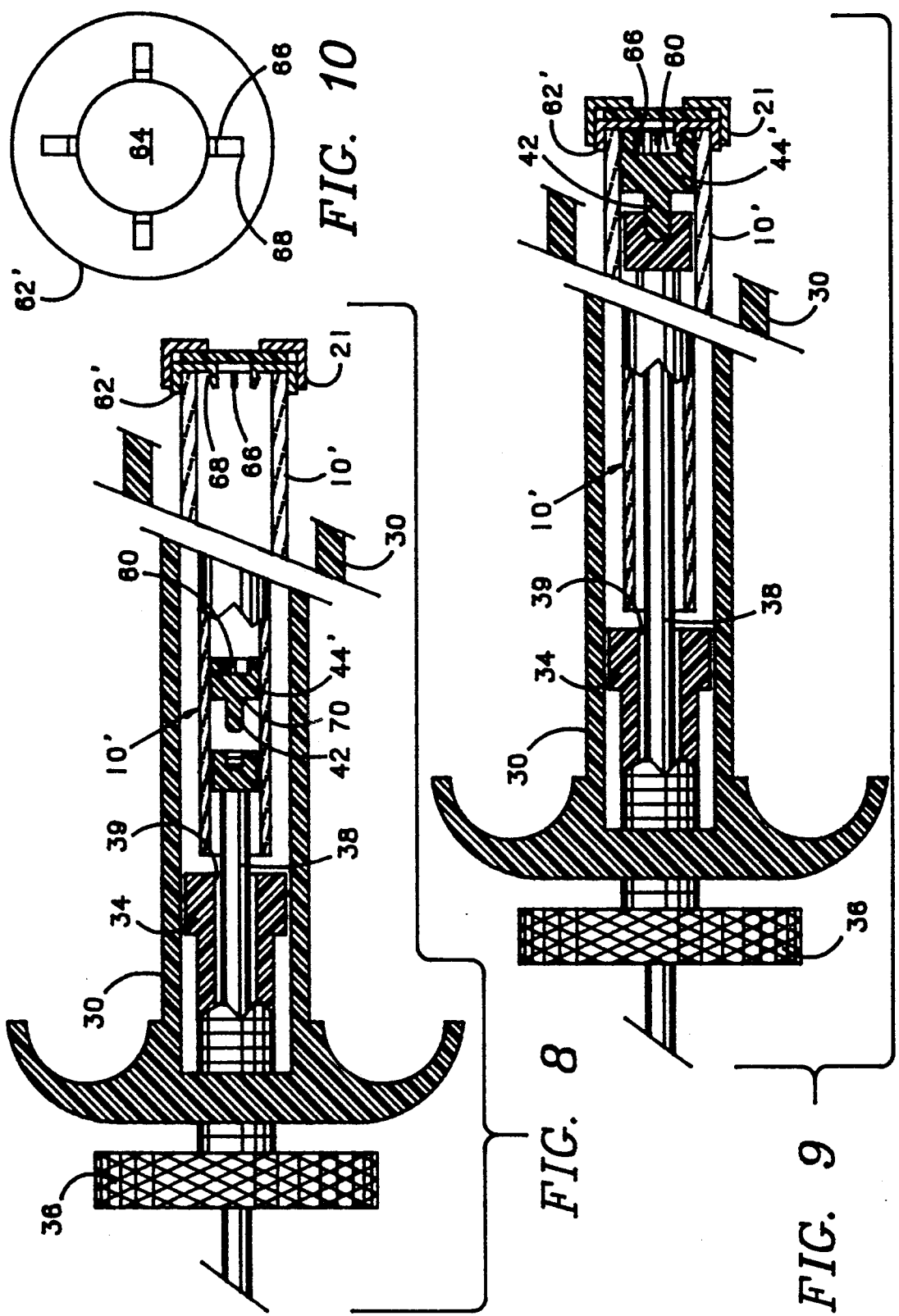

SINGLE USE SYRINGES WITH SECOND USE LOCKOUT

BACKGROUND OF THE INVENTION

This invention relates to medical devices for injecting living bodies and, more particularly, to a single-use hypodermic syringe which locks up after one use comprising, a body having a cylindrical container for holding a fluid; a hollow needle communicating with an interior of the cylindrical container through one end thereof; a sliding plunger disposed in the cylindrical container; a plunger rod communicating with the sliding plunger through an opposite end of the cylindrical container; and, locking means for allowing the sliding plunger to move only in a direction towards the one end whereby after the plunger is moved adjacent the one end, it cannot be withdrawn for subsequent use.

Not so very long ago, hypodermic syringes were of metal and glass. Their use was complicated by the fact that they had to be sterilized between uses as by autoclaving. Recent developments in plastics have made a cheap, disposable syringe for intended single use a practicality. Use of cheap, disposable carpules in a hypodermic syringe holder also offer decided advantages. Since only the carpule and the needle need to be completely sterile, only those parts are replaced in the holder for multiple uses.

The heavy illegal use of injected drugs along with the proliferation of diseases such as hepatitis B and AIDS borne in the body fluids has created a problem where one previously did not exist. Diabetics, hemophiliacs, and the like, employing self-use, disposable needle devices could simply dispose of the devices without fear that they would be put to illicit use. Now, however, there is a need for a way to make such devices truly one-time devices and prevent their subsequent use—without unduly increasing the cost or convenience to the legal users thereof.

Wherefore, it is the object of this invention to provide a way to make disposable and carpule type syringes truly one-time devices and to lock them after first use from any subsequent use.

Other objects and benefits of the invention will become apparent from the detailed description which follows hereinafter when taken in conjunction with the drawing figures which accompany it.

SUMMARY

The foregoing object has been attained in a hypodermic syringe having a body with a cylindrical container for holding a fluid with a hollow needle communicating with the interior of the cylindrical container through one end and a plunger rod communicating with a sliding plunger disposed in the cylindrical container through an opposite end, by the improvement of the present invention for rendering the hypodermic syringe capable of use only one time comprising, a locking member allowing the sliding plunger to move only in a direction towards the one end whereby after the sliding plunger is moved adjacent the one end, it cannot be withdrawn for subsequent use.

In one embodiment, the locking member is carried by the sliding plunger and includes means for gripping interior sidewalls of the cylindrical container to prevent movement of the sliding plunger towards the opposite end. The locking member comprises a flexible, backwards-facing, concave disk having an outside diameter slightly larger than the interior of the cylindrical container whereby the concave disk is wedged into the interior sidewalls of the cylindrical container if movement of the sliding plunger towards the opposite end is attempted. Where the cylindrical container is a carpule releasably held by the body and the plunger rod contains a threaded bore which mates with a threaded extension from the sliding plunger, the threaded extension is connected to the sliding plunger with a weak joint whereby the weak joint separates if force beyond a breaking point of the weak joint is applied to the plunger rod in an attempt to withdraw the sliding plunger towards the opposite end.

In a second embodiment, the locking member is carried by the cylindrical container adjacent the one end and includes means for gripping the sliding plunger to prevent movement of the sliding plunger towards the opposite end. The sliding plunger has in internal bore in an end thereof facing the one end and the locking member includes at least one outward-facing hook which grips internal sidewalls of the internal bore when the sliding plunger is pushed over the hook. Where the cylindrical container is a carpule releasably held by the body and the plunger rod contains a threaded bore which mates with a threaded extension from the sliding plunger, the threaded extension is connected to the sliding plunger with a weak joint whereby the weak joint separates if force beyond a breaking point of the weak joint is applied to the plunger rod in an attempt to withdraw the sliding plunger towards the opposite end.

In a third embodiment, the locking member is carried by the body and comprises means for allowing the plunger rod to only move in one direction. The locking member comprises a locking disk having the plunger rod passing therethrough and teeth for digging into and gripping the plunger rod when movement of the plunger rod towards the opposite end is attempted.

DESCRIPTION OF THE DRAWINGS

FIG. 1 is a partially cutaway exploded drawing of the components of a prior art carpule approach to hypodermic syringes.

FIG. 2 is a partially cutaway drawing of the components of FIG. 1 mounted in a prior art carpule-holding hypodermic syringe.

FIG. 3 is a partially cutaway drawing of the components of FIG. 1 mounted in the prior art carpule-holding hypodermic syringe of FIG. 2 wherein the carpule has been modified according to the present invention to prevent the subsequent use thereof according to a first approach.

FIG. 4 is an enlarged, cutaway drawing of the plunger employed in the carpule of FIG. 3.

FIG. 5 is a partially cutaway drawing of a prior art, disposable hypodermic syringe.

FIG. 6 is a partially cutaway drawing of the disposable hypodermic syringe of FIG. 5 modified according to the present invention to prevent the subsequent use thereof according to a first approach.

FIG. 7 is a partially cutaway drawing of the disposable hypodermic syringe of FIG. 5 modified according to the present invention to prevent the subsequent use thereof according to a second approach.

FIG. 8 is a partially cutaway drawing of the components of FIG. 1 mounted in the prior art carpule-holding hypodermic syringe of FIG. 2 wherein the carpule has been modified according to the present invention to prevent the subsequent use thereof according to a second approach shown prior to use.

FIG. 9 is a partially cutaway drawing of the components of FIG. 1 mounted in the prior art carpule-holding hypodermic syringe of FIG. 2 wherein the carpule has been modified according to the present invention to prevent the subsequent use thereof according to a second approach shown after use and locked.

FIG. 10 is an enlarged plan view of the locking disk employed in the embodiment of FIGS. 8 and 9.

DESCRIPTION OF THE PREFERRED EMBODIMENTS

The problem of carpule type devices will be addressed first with reference to FIGS. 1-4. As shown in FIG. 1, the basic elements are a carpule 10 and a two-ended needle assembly 12. The carpule 10 comprises a cylinder 14 of plastic or glass having an open end 16 and a capped end 18. The capped end is closed by a piece of plastic or rubber (not shown) held in place by a collar 20. The two-ended needle assembly 12 comprises a cap 21 sized to fit over the collar 20. A needle 22 having an injection tip 24 on one end and a carpule-piercing tip 26 on the other end is concentrically held by the cap 21. As seen in FIG. 1, the carpule-piercing tip 26 extends to just within the cap 21 while the injection tip 24 is extended for use in its normal fashion. Typically, there is a plastic cover 28 which snugly fits over the injection tip 24 and the needle 22 up to the cap 21. The cover 28 protects the needle 22 and injection tip 24 as well as providing a safe way in which to handle the two-ended needle assembly 12.

In use, the two-ended needle assembly 12 is placed over the capped end 18 of the carpule 10 and the two in combination are disposed in the syringe assembly 30 of FIG. 2 with the cover 28 and needle 22 extending through a hole 32 provided therefor. The syringe assembly 30 has a pressure member 34 threaded through the rear thereof in concentric alignment with the open end 16 of the carpule 10. By turning the knob 36 to tighten the pressure member 34 against the open end 16 of the carpule 10, the carpule 10 is forced against the two-ended needle assembly 12 causing the carpule-piercing tip 26 to pierce the rubber or plastic to the interior of the carpule 10. A plunger rod 38 extends through a concentric bore 39 in the pressure member 34. The inner end of the plunger rod 38 has a threaded concentric bore 40 which mates with a threaded rod 42 extending concentrically backward toward the open end 16 from a plunger member 44 disposed within the carpule 10. By pushing the plunger rod 38 forward to contact the threaded rod 42 and turning it in a tightening direction, the plunger member 44 is temporarily attached to the end of the threaded rod 42. As thus configured, the syringe assembly 30 in combination with the carpule 10 and two-ended needle assembly 12 acts like a normal syringe and can be used to inject fluid contained in the carpule 10 or to withdraw fluids through the needle 22 into the carpule 10. Moreover, they can be used several times and can be disassembled and reassembled for further use.

FIG. 3 shows a modification which can be made to the carpule to render it incapable of use for injection-only purposes more than once. This approach takes the least amount of modification to the carpule 10 and none to the syringe assembly 30. The only change is that the plunger member 44' has the threaded rod 42 replaced with a flexible, backwards-facing, concave disk 46 of a diameter slightly larger than that of the inside of the carpule 10 as best seen in the enlarged, cross-sectional drawing of FIG. 4. Once the plunger member 44' has been inserted into the open end 16 of the carpule 10, it can only move towards the needle 22. There is no threaded rod 42 to which the plunger rod 38 can be threadedly attached. Moreover, if an attempt is made to move the plunger member 44' back towards the open end 16 (as by a thin wire inserted through the needle 22), the disk 46 rubbing against the inside walls of the carpule 10 tends to flatten out and wedge the plunger member 44' in place against movement. Thus, as will be appreciated, this approach is best employed with pre-filled carpules 10 intended for one-time injection use.

Turning for a moment to FIG. 5, a prior art disposable syringe 48 is shown therein as comprising a barrel 50 having an open end 52 into which a cylindrical plug 54 is attached as with a plastic glue or heat/sonic welding. The plug 54 slidably carries a plunger rod 38 having a plunger member 44 attached to the end thereof. The opposite end of the barrel 50 is closed and carries a needle 22 communicating with the interior of the barrel. Thus, the plunger member 44 can be moved in and out with the plunger rod 38 to fill and empty the barrel 50 through the needle 22.

The plunger member 44' of FIGS. 3 and 4 could be employed in the syringe 48 to render it incapable of use for injection-only purposes more than once as with the carpule of FIG. 3. Another approach producing the same end result is shown in FIG. 7. In this case, a locking disk 56 (similar in function to the disk 46 of FIGS. 3 and 4) is captured behind the plug 54 with a second plug 58. The syringe 48' of FIG. 7 could be filled in the normal manner by pulling back on the plunger rod 38 with the second plug 58 and locking disk 56 loose on the plunger rod 38. The second plug 58 and locking disk 56 could then be positioned and permanently attached in place. Note that the locking disk 56 in this case grips the plunger rod 38 at its center rather than the inside of the barrel 50 with its outer periphery as in the case of the disk 46. Thus, the locking disk 56 should be similar to a type well known to those skilled in the art employed for attaching wheels to shafts, and the like, where a center bore has directionally oriented teeth which slip over the shaft in one direction and dig into the shaft in the opposite direction. In this case, it would be the plunger rod 38 which acts in the manner of the shaft in the uni-directional bore of the locking disk 56.

Both the foregoing devices (i.e. the carpule-using syringe assembly 30 of FIG. 2 and the disposable syringe 48 of FIG. 5) can be modified to make them bi-directionally usable for filling before use; but, locking upon use. The way that this can be accomplished with respect to the disposable syringe 48 is shown in FIG. 6. The needle-facing end of the plunger member 44' is provided with a concentric bore 60. Additionally, a toothed locking disk 62 is placed into the barrel 50 before the plunger member 44' and plunger rod 38. The disk 62, like the disk 46, is slightly larger in diameter than the inside diameter of the barrel 50. It also has a central bore 64 therethrough through which fluids can communicate between the needle 22 and the barrel 50. The bore 64 has several prongs 66 about its periphery facing into the barrel 50. The prongs 66 have outward-facing teeth 68 at the ends thereof. The plunger member 44' can be moved within the barrel 50 between the plug 54 and the ends of the prongs 66 for filling purposes. When used to inject the contents of the barrel 50, however, the plunger member 44' is pushed fully into the barrel 50 forcing the bore 60 thereof over the prongs 66. The prongs 66 and the teeth 68 thereof dig into the material of the plunger member 44' locking the toothed locking disk 62 to the plunger member 44'. If the plunger member 44' is thereafter attempted to be withdrawn, it cannot move because of the wedging action of the toothed locking disk 62 against the inside of the barrel 50. If desired, additional security can be obtained by greatly reducing the diameter of the plunger rod 38 where it joins the plunger member 44' at 70 so as to create a weak joint. The weak joint at 70 is sufficiently strong to hold the plunger rod 38 and the plunger member 44' together under normal use; but, is weak enough to separate and disconnect the plunger rod 38 from the plunger member 44' if the toothed locking disk 62 is attached to the plunger member 44'.

This same approach as employed with a carpule is shown in FIGS. 8-10. Again, the plunger member 44' is provided with the needle-facing bore 60. The toothed locking disk 62 of the above-described embodiment could be used with a standard carpule 10. Alternatively, the toothed locking disk 62' could be built into the closed end of the carpule 10' as depicted in the drawing figures. As depicted in FIG. 9, when the plunger member 44' is pushed to the end of the carpule 10', it is locked to the toothed locking disk 62' by the teeth 68. Thereafter, the plunger rod 38 can be unscrewed and be withdrawn. As with the disposable syringe, the threaded rod 42 can be connected to the plunger member 44' with a weak joint 70 so that the two will separate if an attempt is made to withdraw the plunger member 44' after it is locked in place.

Because of the sizes of the components involved, it is preferred that the toothed locking disk in each case will be of a medically-approved metal for such uses, such as stainless steel.

Wherefore, having thus described the present invention, what is claimed is:

1. In a hypodermic syringe having a body with a cylindrical container for holding a fluid with a hollow needle communicating with the interior of the cylindrical container through one end and a plunger rod communicating with a sliding plunger disposed in the cylindrical container through an opposite end, the improvement for rendering the hypodermic syringe capable of use only one time comprising:
   a) the sliding plunger having an internal bore in an end thereof facing the one end; and,
   b) a locking member allowing the sliding plunger to move only in a direction towards the one end whereby after the sliding plunger is moved adjacent the one end, it cannot be withdrawn for subsequent use, wherein said locking member being carried by the cylindrical container adjacent the one end and includes means for gripping the sliding plunger to prevent movement of the sliding plunger towards the opposite end, and wherein the gripping means includes at least one outward-facing hook which grips internal sidewalls of said internal bore when the sliding plunger is pushed over said hook.

2. The improvement for rendering the hypodermic syringe capable of use only one time of claim 1 wherein:
   said locking member is carried by the sliding plunger and includes means for gripping interior sidewalls of the cylindrical container to prevent movement of the sliding plunger towards the opposite end.

3. The improvement for rendering the hypodermic syringe capable of use only one time of claim 2 wherein:
   said locking member comprises a flexible, backwards-facing, concave disk having an outside diameter slightly larger than the interior of the cylindrical container whereby said concave disk is wedged into said interior sidewalls of the cylindrical container if movement of the sliding plunger towards the opposite end is attempted.

4. The improvement for rendering the hypodermic syringe capable of use only one time of claim 2 wherein additionally:
   a) the cylindrical container is a carpule releasably held by the body;
   b) the plunger rod contains a threaded bore which mates with a threaded extension from the sliding plunger; and,
   c) said threaded extension is connected to the sliding plunger with a weak joint whereby said weak joint separates if force beyond a breaking point of said weak joint is applied to the plunger rod in an attempt to withdraw the sliding plunger towards the opposite end.

5. The improvement for rendering the hypodermic syringe capable of use only one time of claim 1 wherein:
   said locking member is carried by the body and comprises means for allowing the plunger rod to only move in one direction.

6. The improvement for rendering the hypodermic syringe capable of use only one time of claim 5 wherein:
   said locking member comprises a locking disk having the plunger rod passing therethrough and teeth for digging into and gripping the plunger rod when movement of the plunger rod towards the opposite end is attempted.

7. In a hypodermic syringe having a body with a cylindrical container for holding a fluid with a hollow needle communicating with the interior of the cylindrical container through one end and a plunger rod communicating with a sliding plunger disposed in the cylindrical container through an opposite end, the improvement for rendering the hypodermic syringe capable of use only one time comprising:
   a) a locking member allowing the sliding plunger to move only in a direction towards the one end whereby after the sliding plunger is moved adjacent the one end, it cannot be withdrawn for subsequent use, wherein said locking member being carried by the cylindrical container adjacent the one end and includes means for gripping the sliding plunger to prevent movement of the sliding plunger towards the opposite end; and wherein further,
   b) the cylindrical container is a carpule releasably held by the body;
   c) the plunger rod contains a threaded bore which mates with a threaded extension from the sliding plunger; and,
   d) said threaded extension is connected to the sliding plunger with a weak joint whereby said weak joint separates if force beyond a breaking point of said weak joint is applied to the plunger rod in an attempt to withdraw the sliding plunger towards the opposite end.

8. The single-use hypodermic syringe of claim 1 wherein:
   said locking member is carried by said sliding plunger and includes means for gripping interior sidewalls of said cylindrical container to prevent movement of said sliding plunger towards said opposite end.

9. The single-use hypodermic syringe of claim 8 wherein:

said locking member comprises a flexible, backwards-facing, concave disk having an outside diameter slightly larger than said interior of said cylindrical container whereby said concave disk is wedged into said interior sidewalls of said cylindrical container if movement of said sliding plunger towards said opposite end is attempted.

10. The single-use hypodermic syringe of claim 8 wherein additionally:
 a) said cylindrical container is a carpule releasably held by said body;
 b) said plunger rod contains a threaded bore which mates with a threaded extension from said sliding plunger; and,
 c) said threaded extension is connected to said sliding plunger with a weak joint whereby said weak joint separates if force beyond a breaking point of said weak joint is applied to said plunger rod in an attempt to withdraw said sliding plunger towards said opposite end.

11. The single-use hypodermic syringe capable of use only one time of claim 1 wherein:

said locking member is carried by said cylindrical container adjacent said one end and includes means for gripping said sliding plunger to prevent movement of said sliding plunger towards said opposite end.

12. The single-use hypodermic syringe capable of use only one time of claim 1 wherein:

said locking member is carried by said body and comprises means for allowing said plunger rod to only move in one direction.

13. The single-use hypodermic syringe capable of use only one time of claim 12 wherein:

said locking member comprises a locking disk having said plunger rod passing therethrough and teeth for digging into and gripping said plunger rod when movement of said plunger rod towards said opposite end is attempted.

14. A single-use hypodermic syringe which locks up after one use comprising:
 a) a body having a cylindrical container for holding a fluid;
 b) a hollow needle communicating with an interior of said cylindrical container through one end thereof;
 c) a sliding plunger disposed in said cylindrical container, wherein said sliding plunger has in internal bore in an end thereof facing said one end;
 d) a plunger rod communicating with said sliding plunger through an opposite end of said cylindrical container; and,
 e) locking means allowing said sliding plunger to move only in a direction towards said one end whereby after said plunger is moved adjacent said one end, it cannot be withdrawn for subsequent use, wherein said locking means is carried by said cylindrical container adjacent said one end and includes means for gripping said sliding plunger to prevent movement of said sliding plunger towards said opposite end, and wherein the gripping means includes at least one outward-facing hook which grips internal sidewalls of said internal bore when said sliding plunger is pushed over said hook.

15. A single-use hypodermic syringe which locks up after one use comprising:
 a) a body having a cylindrical container for holding a fluid, wherein said cylindrical container is a carpule releasably held by said body;
 b) a hollow needle communicating with an interior of said cylindrical container through one end thereof;
 c) a sliding plunger disposed in said cylindrical container;
 d) a plunger rod communicating with said sliding plunger through an opposite end of said cylindrical container, wherein said plunger rod contains a threaded bore which mates with a threaded extension from said sliding plunger and, said threaded extension is connected to said sliding plunger with a weak joint whereby said weak joint separates if force beyond a breaking point of said weak joint is applied to said plunger rod in an attempt to withdraw said sliding plunger towards said opposite end; and,
 e) locking means allowing said sliding plunger to move only in a direction towards said one end whereby after said plunger is moved adjacent said one end, it cannot be withdrawn for subsequent use, wherein said locking means is carried by said cylindrical container adjacent said one end and includes means for gripping said sliding plunger to prevent movement of said sliding plunger towards said opposite end.

16. In a carpule-using hypodermic syringe having a body which releasably holds a carpule with a hollow needle communicating with the interior of the carpule through one end and a plunger rod communicating with a sliding plunger disposed in the carpule through an opposite end, a single-use carpule capable of use only one time comprising:
 a) a cylindrical carpule having internal sidewalls;
 b) a locking member disposed within said cylindrical carpule allowing the sliding plunger to move only in a direction towards the one end whereby after the sliding plunger is moved adjacent the one end, it cannot be withdrawn for subsequent use, wherein said locking member is carried by the sliding plunger and includes means for gripping said interior sidewalls of said cylindrical carpule to prevent movement of the sliding plunger towards the opposite end;
 c) the plunger rod contains a threaded bore which mates with a threaded extension from the sliding plunger; and,
 d) said threaded extension is connected to the sliding plunger with a weak joint whereby said weak joint separates if force beyond a breaking point of said weak joint is applied to the plunger rod in an attempt to withdraw the sliding plunger towards the opposite end.

17. The single-use carpule for rendering a hypodermic syringe capable of use only one time of claim 1 wherein:

said locking member comprises a flexible, backwards-facing, concave disk having an outside diameter slightly larger than said interior sidewalls of said cylindrical carpule whereby said concave disk is wedged into said interior sidewalls of said cylindrical carpule if movement of the sliding plunger towards the opposite end is attempted.

18. In a carpule-using hypodermic syringe having a body which releasably holds a carpule with a hollow needle communicating with the interior of the carpule through one end and a plunger rod communicating with a sliding plunger disposed in the carpule through an opposite end, a single-use carpule capable of use only one time comprising:

a) a cylindrical carpule having internal sidewalls;

b) the sliding plunger has an internal bore in an end thereof facing the one end; and, c) a locking member disposed within said cylindrical carpule allowing the sliding plunger to move only in a direction towards the one end whereby after the sliding plunger is moved adjacent the one end, it cannot be withdrawn for subsequent use, wherein said locking member is carried by said cylindrical carpule adjacent the one end and includes at least one outward-facing hook which grips internal sidewalls of said internal bore when the sliding plunger is pushed over said hook.

19. In a carpule-using hypodermic syringe having a body which releasably holds a carpule with a hollow needle communicating with the interior of the carpule through one end and a plunger rod communicating with a sliding plunger disposed in the carpule through an opposite end, a single-use carpule capable of use only one time comprising:

a) a cylindrical carpule having internal sidewalls;

b) a locking member disposed within said cylindrical carpule allowing the sliding plunger to move only in a direction towards the one end whereby after the sliding plunger is moved adjacent the one end, it cannot be withdrawn for subsequent use, wherein said locking member is carried by said cylindrical carpule adjacent the one end and includes means for gripping the sliding plunger to prevent movement of the sliding plunger towards the opposite end;

c) the plunger rod contains a threaded bore which mates with a threaded extension from the sliding plunger; and, d) said threaded extension is connected to the sliding plunger with a weak joint whereby said weak joint separates if force beyond a breaking point of said weak joint is applied to the plunger rod in an attempt to withdraw the sliding plunger towards the opposite end.

* * * * *